United States Patent
Martin

(10) Patent No.: US 12,196,671 B2
(45) Date of Patent: Jan. 14, 2025

(54) METHOD FOR CLASSIFICATION OF AN EDIBLE SEED AND A SCANNING DEVICE THEREFOR

(71) Applicant: SURENUT PTY LTD, Renmark (AU)

(72) Inventor: Tom Martin, Renmark (AU)

(*) Notice: Subject to any disclaimer, the term of this patent is extended or adjusted under 35 U.S.C. 154(b) by 115 days.

(21) Appl. No.: 17/787,676

(22) PCT Filed: Dec. 15, 2020

(86) PCT No.: PCT/AU2020/051370
§ 371 (c)(1),
(2) Date: Jun. 21, 2022

(87) PCT Pub. No.: WO2021/134110
PCT Pub. Date: Jul. 8, 2021

(65) Prior Publication Data
US 2022/0412884 A1  Dec. 29, 2022

Related U.S. Application Data

(60) Provisional application No. 62/954,561, filed on Dec. 29, 2019.

(30) Foreign Application Priority Data

Nov. 23, 2020  (AU) ................ 2020904310

(51) Int. Cl.
*G01N 21/359* (2014.01)
*A23L 5/20* (2016.01)
(Continued)

(52) U.S. Cl.
CPC .............. *G01N 21/359* (2013.01); *A23L 5/20* (2016.08); *B07C 5/3425* (2013.01); *G01J 3/108* (2013.01);
(Continued)

(58) Field of Classification Search
CPC .. G01N 21/359; G01N 21/3563; G01N 33/02; G01N 21/94; G01N 2021/8466;
(Continued)

(56) References Cited

U.S. PATENT DOCUMENTS 6,100,526 A    8/2000  Mayes
2010/0198397 A1  8/2010  Berghmans
(Continued)

FOREIGN PATENT DOCUMENTS

AT         525827 A1  *  8/2023
WO    WO-2019201786 A1  *  10/2019  ........... B07C 5/3425

OTHER PUBLICATIONS

Kandpal et al., Short wave infrared (SWIR) hyperspectral imaging technique for examination of aflatoxinB1(AFB1) on corn kernels., 2015, Food Control vol. 51, pp. 171-176. (Year: 2015).*
(Continued)

*Primary Examiner* — Christine S. Kim

(57) ABSTRACT

A method and system for detecting an aflatoxin on a grain, seed or nut which includes sorting a plurality of the grain seeds in single file, capturing a plurality of shortwave infrared images of each seed, comparing the wavelengths from the captured image with the wavelengths indicative of an aflatoxin presence at a predetermined concentration, and ejecting from a group of the seeds those seeds that have an aflatoxin concentration greater than the predetermined concentration as indicated by the wavelengths from the captured images.

4 Claims, 6 Drawing Sheets

(51) Int. Cl.
*B07C 5/342* (2006.01)
*G01J 3/10* (2006.01)
*G01N 21/3563* (2014.01)
*G01N 21/84* (2006.01)
*G01N 21/85* (2006.01)
*G01N 21/94* (2006.01)
*G01N 33/02* (2006.01)
*G06V 10/143* (2022.01)
*G06V 10/58* (2022.01)
*G06V 20/68* (2022.01)

(52) U.S. Cl.
CPC ......... *G01N 21/3563* (2013.01); *G01N 33/02* (2013.01); *G06V 10/143* (2022.01); *G01N 2021/8466* (2013.01); *G01N 2021/8592* (2013.01); *G01N 21/94* (2013.01); *G06V 10/58* (2022.01); *G06V 20/68* (2022.01)

(58) Field of Classification Search
CPC ........... G01N 2021/8592; G01N 33/10; G01N 2201/1296
See application file for complete search history.

(56) References Cited

U.S. PATENT DOCUMENTS

| | | |
|---|---|---|
| 2011/0089090 A1 | 4/2011 | Nierle et al. |
| 2011/0094946 A1 | 4/2011 | Prystupa et al. |
| 2012/0061586 A1* | 3/2012 | Yao ................. G01N 21/6486 250/461.1 |

OTHER PUBLICATIONS

Wu et al., Determination of toxigenic fungi and aflatoxins in nuts and dried fruits using imaging and spectroscopic techniques, published in 2018, Food Chemistry, vol. 252, pp. 228-242. (Year: 2018).*

Cogdill et al., Single-Kernel Maize Analysis by Near-Infrared Hyperspectral Imaging, 2004, vol. 47, pp. 311-320 (Year: 2004).*

Lohumi et al., Raman hyperspectral imaging and spectral similarity analysis for quantitative detection of multiple adulterants in wheat flour, Mar. 28, 2019, Biosystems Engineering, vol. 181, pp. 103-113. (Year: 2019).*

Sato et al., Nondestructive determination of Fatty Acid Composition of Husked Sunflower Seeds by Near Infrared Spectroscopy, 1995, JAOCS, vol. 72, pp. 1177-1183 (Year: 1995).*

International Search Report (ISR) (form 210) corresponding to counterpart International Patent Application PCT/AU2020/051370, mailed Feb. 5, 2021.

Written Opinion of the International Searching Authority (WO/ISA) (form 237) corresponding to counterpart International Patent Application PCT/AU2020/051370, mailed Feb. 5, 2021.

Chu X. et al., "Detection of aflatoxin B1 (AFB1) in individual maize kernels using short wave infrared (SWIR) hyperspectral imaging", Biosystems Engineering, 2017, vol. 157, pp. 13-23. [Published online Mar. 6, 2017].

* cited by examiner

METHOD FOR CLASSIFICATION OF AN EDIBLE SEED AND A SCANNING DEVICE THEREFOR

This application is a national phase of International Application No. PCT/AU2020/051370 filed Dec. 15, 2020, which claims the benefit of U.S. Provisional Application No. 62/954,561 filed Dec. 29, 2019, in the U.S. Patent Office and claims priority to Australian Application No. 2020904310 filed on Nov. 23, 2020, in the Australian Patent Office, which are hereby incorporated herein by reference.

FIELD OF INVENTION

The present disclosure relates to a method and system for classification of an edible grain seed using electromagnetic radiation. While an application of the present disclosure is in the classification of edible seeds, it could equally well be applied to the classification of any foodstuff for human and/or animal consumption.

BACKGROUND OF INVENTION

Aflatoxin is a known carcinogen globally affecting over 25% of crops mainly tree nuts, peanuts, maize, cottonseed. Over 4 billion people worldwide are exposed to dietary aflatoxins. It is estimated that between 5-28% of liver cancers in humans could be attributed to aflatoxins. Every season, almond-processors detect out-of-specification product on receipt, which then must be diverted from sale for human consumption as there is no effective means of eliminating aflatoxins from almonds without significant damage to the product. This removal and reduction in potential return results in large losses.

Due to stringent food safety regulations, including a low contamination threshold for carcinogenic fungal aflatoxins, many countries require almond shipments to be certified. Industry standard processes for grading and testing harvested almonds are labour-intensive, time consuming, and expensive. With manual inspection, it is impossible to identify low levels of contaminants such as aflatoxins, which have very low tolerance in food products (below 5 ppb). In Australia and other major nut-producing countries, composition and safety evaluations are conducted using wet lab analyses. Wet chemical analysis for aflatoxin screening of almonds is destructive, slow, and expensive. Accordingly, there is a need for an alternative and automated almond classification method, which is rapid, objective, non-destructive, consistent, and accurate, and a scanning device useful in such a method.

Australia is the second largest producer of almonds after the United States of America. Australian almonds are exported both as kernel (71%) and inshell (29%). Most of the almond production in Australia is concentrated in the Riverland, Sunraysia and Riverina regions. The Australian almond industry contributes significantly to the local communities both socially and economically in almond growing and processing regions.

To deliver optimum product quality, almond kernels are sampled regularly (typically every one tonne bin) from the processing line and manually inspected to assign an appropriate commercial grade. However, manual sampling is labour intensive, slow and subjective which may lead to inconsistent and inaccurate grading. Also, food safety is increasingly becoming an important issue in the almond market like in other food commodities.

Due to stringent food safety regulations, including a low contamination threshold for carcinogenic fungal aflatoxins, many countries require almond shipments to be certified. Industry standard processes for grading and testing harvested almonds are labour-intensive, time consuming, and expensive. In Australia and other major nut producing countries, composition and safety evaluations are conducted using wet lab analyses. Depending on the season as much as 15% of the total Australian crop could be "out-of-spec" for mycotoxins. By detecting levels of aflatoxin early in the processing phase, informed decisions can be made—directing affected almonds to markets that require forms of heat treatment such as roasting and blanching, which can lower aflatoxin levels to allow entry to some markets.

The European Union presently enforces a regulation that limits the total aflatoxin content in ready-to-eat almonds to a maximum level of 10 $\mu g\ kg^{-1}$ (Commission Regulation (EC) No. 1881/2006 amended by Commission Regulation (EU) No. 165/2010), while the U.S. Food and Drug Administration (USFDA) maintains a 20 $\mu g\ kg^{-1}$ threshold. The distribution of aflatoxins in agricultural products has a high level of randomness because mould growth is dependent on many variables, including humidity, wind, shade, and other factors. The random distribution of aflatoxin in harvested crops is further increased due to multiple handling operations and processes, including partially or fully automated operations and processes. There are two primary existing methods for aflatoxin detection: liquid chromatography (LC) and UV fluorescence. Liquid chromatography is a destructive laboratory testing method useful for extracting and separating aflatoxins to determine an aflatoxin concentration of the input product. Since laboratory methods of detection require the sample to be ground up and chemically treated, in a sense destroying the product, test validation is limited. Therefore, the usefulness of the method to remove contaminated nuts from a larger quantity is limited. Moreover, diversity and abundance of aflatoxin demands higher number of samples need to destroyed during analysis, which leads to wastage of the huge number of almonds.

Aflatoxin is fluorescent substance. Specifically, aflatoxin can be detected around a 435 nm wavelength when exposed to UV light at 365 nm. However, the whiter the substrate, the easier the recognition of aflatoxin from the image. The coloured skin of certain foodstuffs, such as the brown skin of almonds cancels the effect of fluorescence from aflatoxin and impedes the effective use of UV light for detection of aflatoxin. Additionally, the brown surface of almonds produces fluorescence response at high spectrum levels from any applied light source with a large shift of frequency. Therefore, what is needed is a rapid, non-destructive, reliable and accurate detection and measurement of aflatoxin for the almond industry.

It will be clearly understood that, if a prior art publication is referred to herein, this reference does not constitute an admission that the publication forms part of the common general knowledge in the art in Australia or in any other country.

SUMMARY

The present disclosure in one aspect sets out a method for classifying a foodstuff. The foodstuff may be an edible grain seed. The method may include illuminating the edible seed with at least one wavelength of electromagnetic radiation, the at least one wavelength of electromagnetic radiation is partially reflected by each nut/seed including specific signals from aflatoxin if it is present, detecting the reflected signal to provide a detected aflatoxin signal, comparing the detected aflatoxin signal with predetermined reflectance levels from known concentrations of aflatoxin to provide the first accurate measurement of aflatoxin concentrations, and classifying the edible seed aflatoxin concentration.

The present disclosure in another aspect sets out a scanning device for classifying a foodstuff. The foodstuff may be an edible grain seed or nut. The scanning device may include a reservoir configured to hold at least one edible seed, a chute, having at least one electromagnetic radiation source to illuminate the seed with at least three wavelengths of electromagnetic radiation, the at least three wavelengths of electromagnetic radiation causing a reflection signal of at least one type of aflatoxin, a camera configured to detect the reflected light, a filter to remove extraneous reflections, and to provide the aflatoxin signal; and a microprocessor configured to: compare the detected aflatoxin signal with predetermined signals of known concentration of the at least aflatoxin to provide a first calibrated measurement of aflatoxin concentration, and classify the edible seed relative to the first measured aflatoxin concentration, accurate to +/−0.16 µg.

Foodstuff for human consumption and/or animal consumption must be kept dry and free from mould to reduce the risks associated with contamination. It is not always possible to eliminate the growth of mould on foodstuff and, accordingly, it would be beneficial to have a method of classifying the level of contamination of a foodstuff by a mould, for example *Aspergillus* sp.

Foodstuff for human consumption that may be contaminated by mould under inappropriate storage conditions includes edible seeds, cereals, fruits, and vegetables. Foodstuff for animal consumption that may be contaminated by mould under inappropriate storage conditions include hay, fodder, feed grains, animal feed pellets, animal feed crumbles, and animal feed mixes.

In another preferred embodiment, the present disclosure relates to a method for detecting an aflatoxin on a grain seed. The method includes sorting a plurality of grain seeds or nuts in a single file array; capturing a plurality of shortwave infrared images of each grain seed; comparing wavelengths from the captured image with wavelengths indicative of an aflatoxin presence at a predetermined concentration; and ejecting from the plurality of grain seeds those grain seeds that have an aflatoxin concentration greater than the predetermined concentration as indicated by the wavelengths from the captured images.

In another preferred embodiment, the present disclosure relates to a system for determining when a grain seed has an unsafe concentration of aflatoxin. The system includes a grain seed reservoir; a chute from the reservoir to a rotating glass disc; a plurality of light sources configured to emit a suppressed visible light upon each gain seed; and a plurality of hyperspectral cameras configured to each capture a plurality of spectral images of each grain seed. The system also includes a processor configured to align and segment a spectral cube, determine an average reflectance for each spectral image, compare the average reflectance with a predetermined reflectance value indicative of a presence of an aflatoxin concentration designated to fail a predetermined health standard, and send instructions to a diverter to separate a grain seed determined to fail the health standard.

It is to be understood that both the foregoing general description and the following detailed description are exemplary and explanatory only and are not restrictive of the invention, as claimed. In the present specification and claims, the word "comprising" and its derivatives including "comprises" and "comprise" include each of the stated integers but does not exclude the inclusion of one or more further integers.

It will be appreciated that reference herein to "preferred" or "preferably" is intended as exemplary only.

The claims as filed and attached with this specification are hereby incorporated by reference into the text of the present description. The accompanying drawings, which are incorporated in and constitute a part of this specification, illustrate several embodiments of the invention and together with the description, explain the principles of the invention.

DETAILED DESCRIPTION

Figure 1:
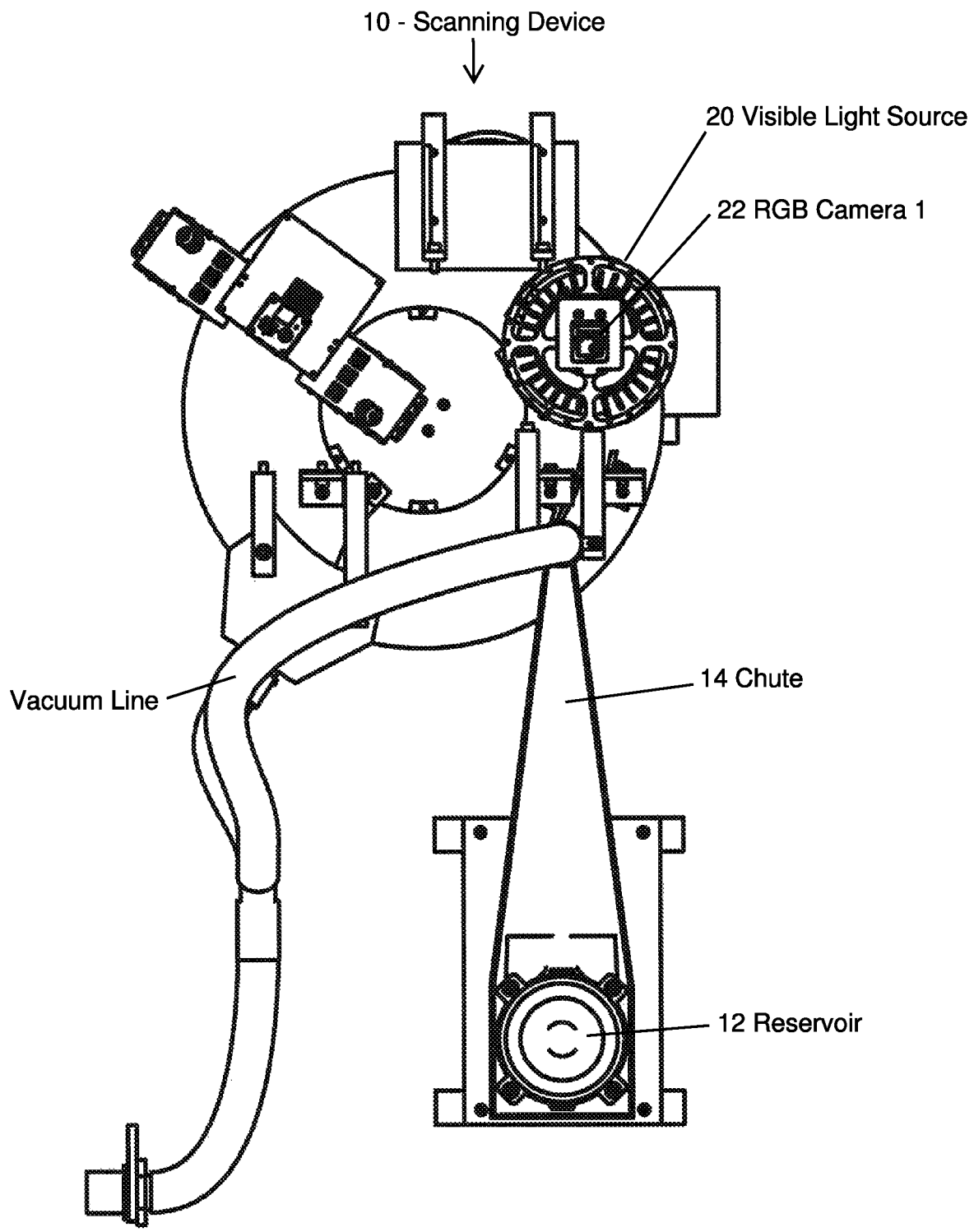
FIG. 1 is a top view of a scanning device in accordance with a preferred embodiment of the present disclosure.
Figure 2:
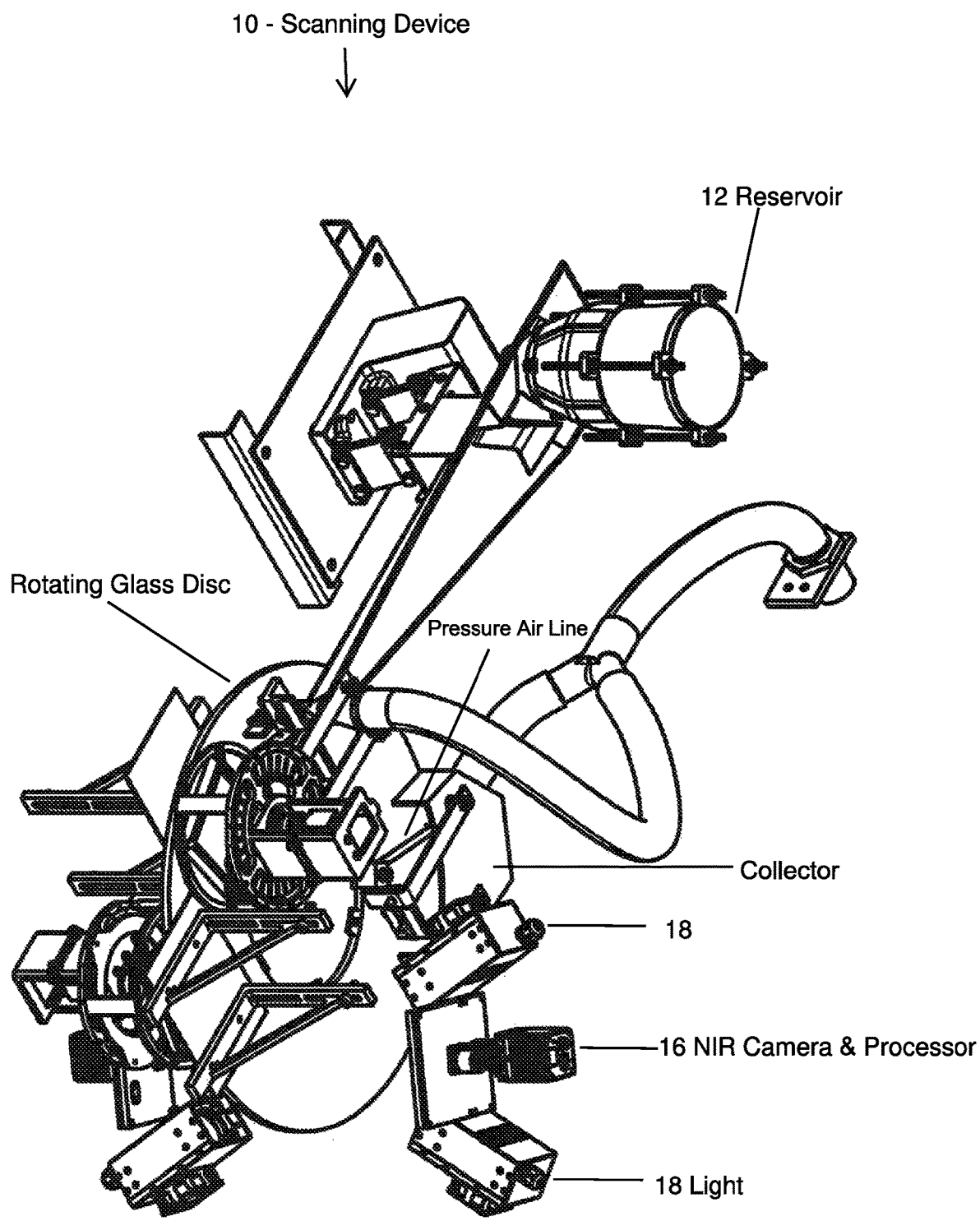
FIG. 2 is a front view of the scanning device of FIG. 1.
Figure 3:
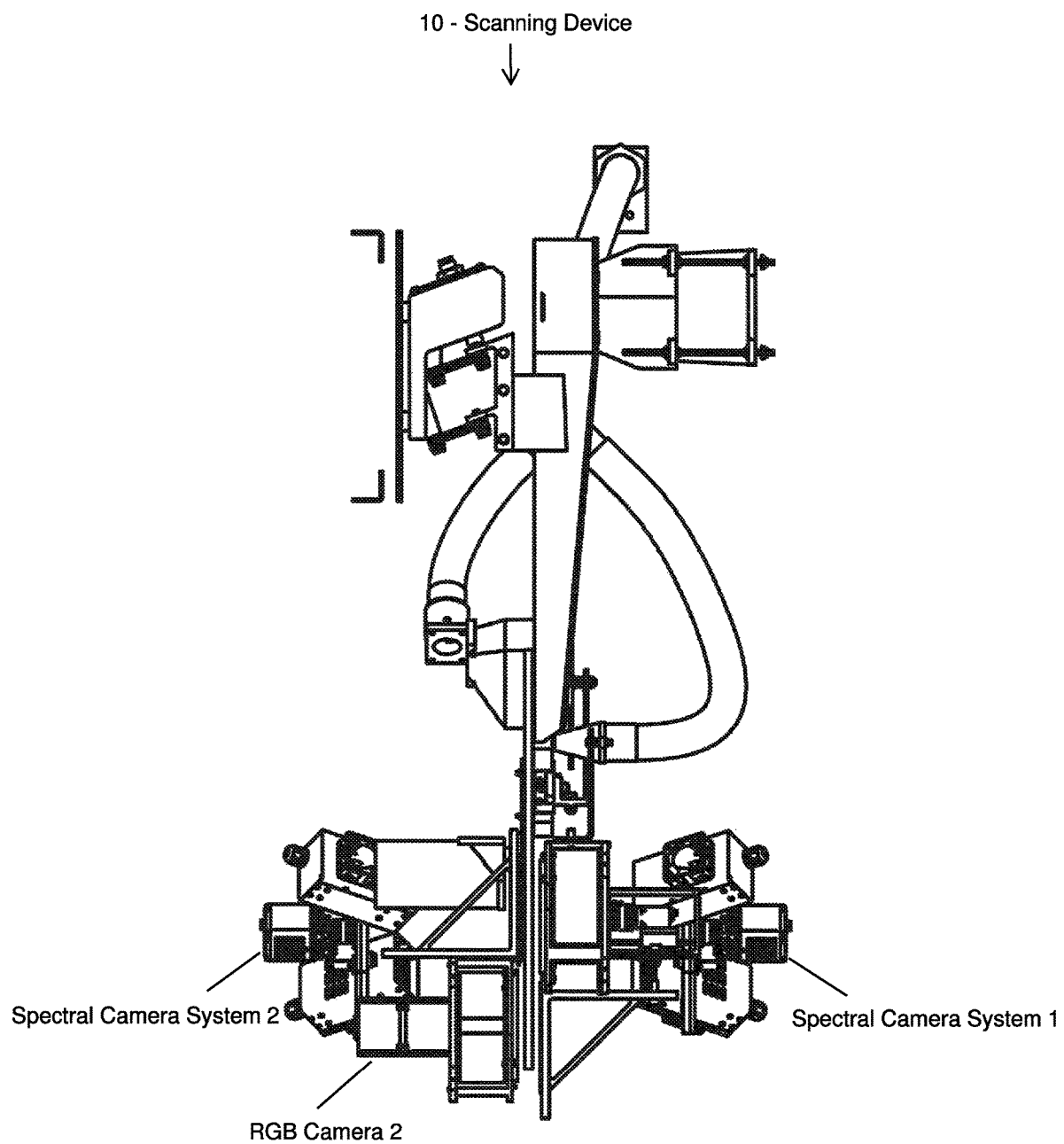
FIG. 3 is another side view of the scanning device of FIG. 1.
Figure 4:
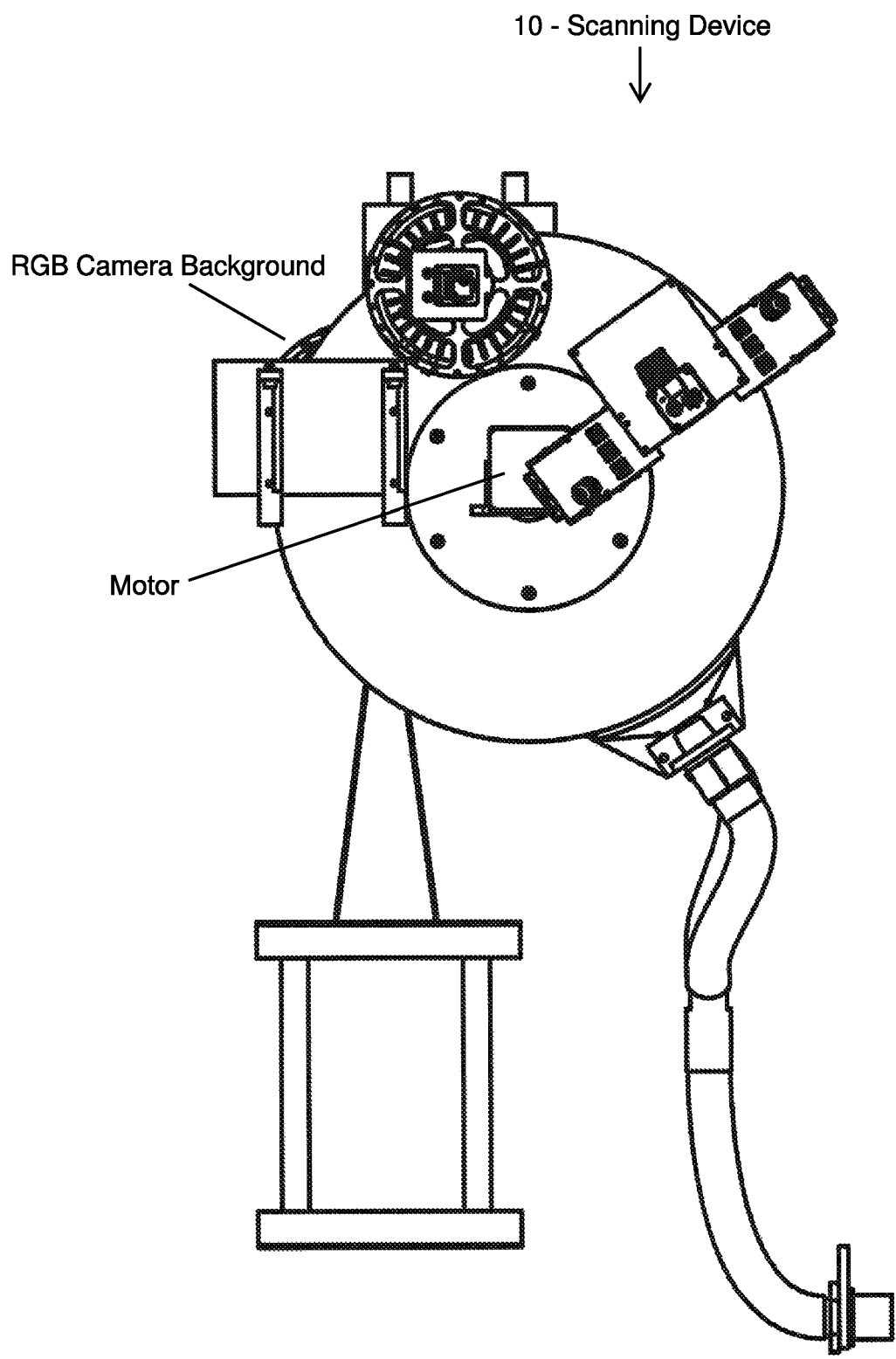
FIG. 4 is a bottom view of the scanning device of FIG. 1.
Figure 5:
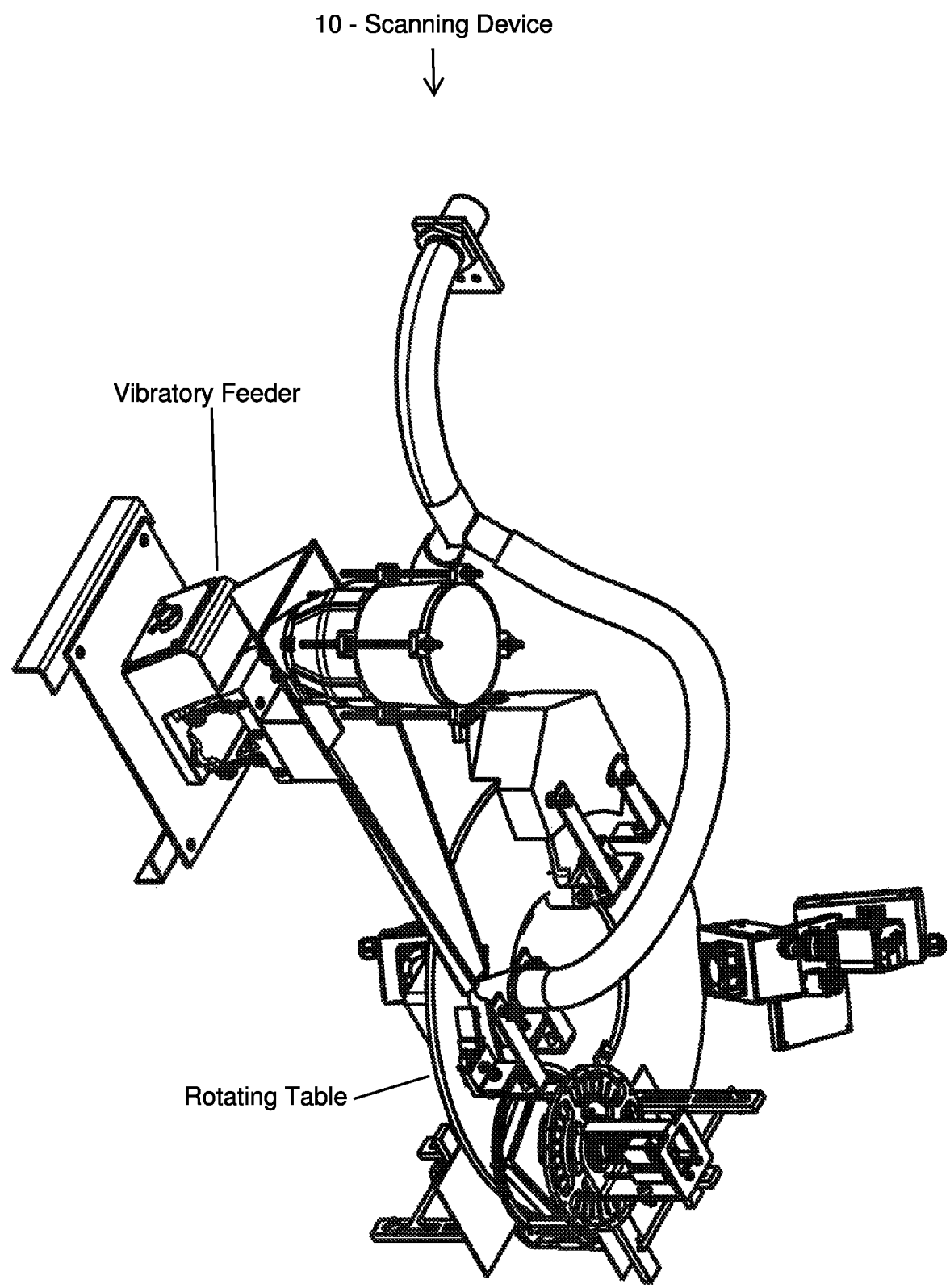
FIG. 5 is a perspective view of the scanning device of FIG. 1.

Reference will now be made in detail to the present preferred embodiments of the invention, examples of which are illustrated in the accompanying drawings.

FIGS. 1 to 5 show a preferred embodiment of a scanning device 10. The preferred elements of scanning device 10 and their interrelationships are described below. Scanning device 10 includes a reservoir 12, a chute 14, a near infrared (NIR) camera detector 16, and a microprocessor. Reservoir 12 is configured to hold at least one edible seed. Scanning device 10 has at least one electromagnetic radiation source 18. In use, the electromagnetic radiation source 18 illuminates the edible seed with at least one wavelength of electromagnetic radiation. At specific wavelengths of NIR radiation, the reflectance can be measured and after calibration the detection of at least one type of aflatoxin can be accurately measured. An NIR camera 16 is configured to capture any reflected light. The microprocessor is configured to compare the various wavelengths of this reflectance and accurately measure any levels of aflatoxin that may be present by comparison with previous calibrations from accurately laboratory dosed specimens. A signal detector 16 is a near infrared (NIR) hyperspectral camera. Near infrared (NIR) hyperspectral cameras can detect internal defects which are not visible to human eyes or to cameras operating in the visible region of the electromagnetic spectrum. This enables the detection and classification of aflatoxins.

Scanning device 10 further includes a visible light source 20 and a visible light detector 22. Visible light source 20 illuminates the edible seed and visible light detector 22 detects an image of the edible seed. In a preferred embodiment, visible light source 20 is a halogen light source. The microprocessor is configured to detect a blemish on a surface of the edible seed as shown in the image, compare the blemish to a predetermined blemish signal of a known concentration of the aflatoxin to provide a second estimated aflatoxin concentration, and classify the edible seed relative to the second estimated aflatoxin concentration.

Preferably, the image has a dimension approximately four times the width of the edible seed. Further preferably, visible light detector 22 is an RGB light camera. In a further preferred embodiment, scanning device 10 includes a hygrometer to measure moisture content of the edible seed. The hygrometer may be an optical hygrometer. Preferably, the hygrometer is a differential absorption hygrometer.

RGB cameras are used on each side of the glass plate and NIR cameras, from only one side. Many wavelengths may be used depending upon the characteristic being investigated, for example aflatoxin, FFA, PV, and moisture.

Moisture content, rancidity-free fatty acids (FFA) and peroxide value (PV) are good quality indicators of almonds and industry use this data to inform product shelf life. Rancidity and aflatoxin have significant effect on consumer health. The four major and naturally known aflatoxins are produced by the *Aspergillus* species of mould. Aflatoxin $B_1$ (AFB1), aflatoxin $B_2$ (AFB2), aflatoxin $G_1$ (AFG1) and aflatoxin $G_2$ (AFG2) are predominantly encountered, with AFB1 being the most common and the most potent genotoxic and carcinogenic of the aflatoxins. Detectable aflatoxins can be produced by *Aspergillus flavus* or *Aspergillus parasiticus*.

The edible seed may be, for example only, an almond, a Brazil nut, a candlenut, a cashew, a Chilean hazelnut, a hazelnut, a macadamia, a peanut, a pecan, a pine nut, a pistachio, or a walnut.

It will be appreciated that the scanning device 10 and the reservoir 12 may be configurable to accommodate any foodstuff suitable for human and/or animal consumption. A plurality of images of each edible seed is compiled, preferably using a virtual cube, to provide a composite 3D representation of the edible seed. Artificial intelligence, i.e., deep learning, including forward selection and backward elimination, stepwise selection, etc., is employed to discern all fault parameters of the edible seed. Where more than one fault is present on an edible seed, the suitability determination is determined by what is least desirable for the final consumer to experience/taste—that is fault parameters are ranked.

The edible seeds can be sorted to achieve desired specifications for the edible seeds, e.g., edible seeds can be categorised for human or animal consumption, for meal, crushed nuts, or nut milk production. The data produced from this analyser determination informs down the line managers in sorting, processing and marketing. If desired, the system can be linked to digital sorting machines to enhance performance to be focused only on customer specifications.

The scanning device can be connected to a network or the internet for online management and/or reporting. The scanning device may include at least one glass plate for the edible seed to be supported and/or conveyed across. The scanning device may include a mechanism to clean the glass plate. Alternatively, the glass plate may be electrically charged to repel dust particles. It will be appreciated that a dust particle may include a fibre, particulate organic material, or the like. Such particulate organic material may originate from the edible seed.

Referring to FIGS. 1 to 5, a preferred method for classifying an edible seed is described below. The method includes illuminating the edible seed with a number of wavelengths of NIR electromagnetic radiation. The reflectance of electromagnetic radiation from the seed is then analysed and compared to the reflectance generated by seeds dosed at known rates of aflatoxin in a laboratory. The calibration used is preferably measuring Aflatoxin $B_1$ to +/−0.16 μg/g.

Preferably, the wavelength of electromagnetic radiation is near infrared radiation.

The aflatoxin may be produced by *Aspergillus* sp. More particularly, the aflatoxin may be produced by *Aspergillus flavus Aspergillus parasiticus*. Preferably, the detectable aflatoxin is at least one of aflatoxin $B_1$, aflatoxin $B_2$, aflatoxin $G_1$, or aflatoxin $G_2$.

It will be appreciated that the steps described above may be performed in a different order, varied, or some steps omitted entirely without departing from the scope of the present invention.

Figure 6:
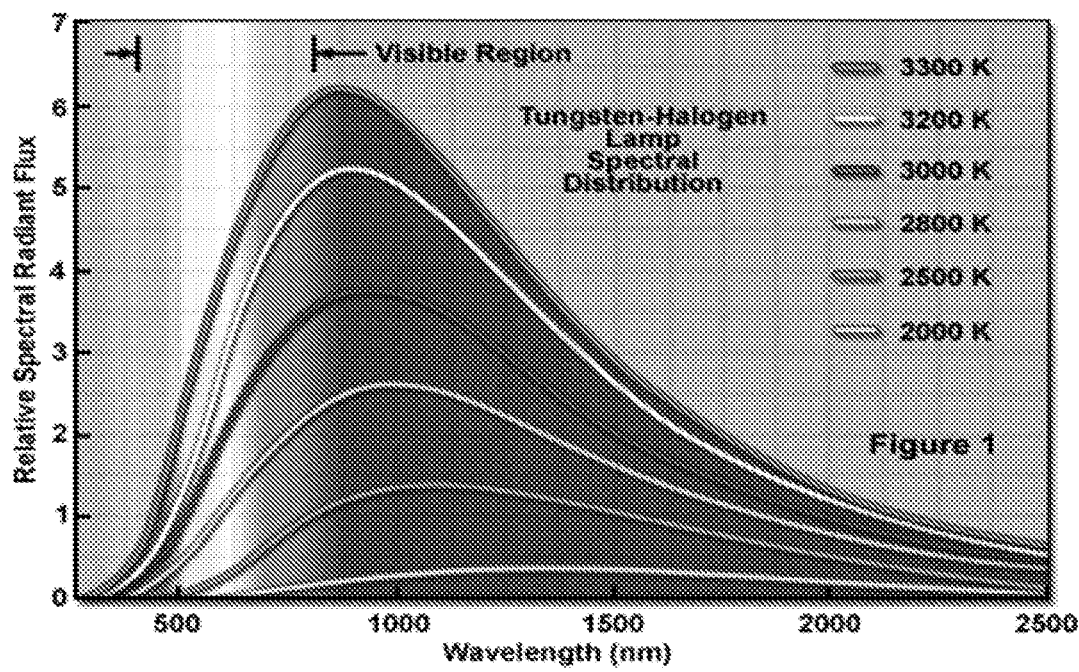
FIG. 6 is an image comparing spectral radiant flux with wavelength.

FIG. 6 shows a full spectrum, with visible light range as indicated. Hyperspectral imaging is a combination of both spatial imaging and spectroscopy (spectral). The hyperspectral images are three—dimensional arrays (m× n× λ), where m and n are the spatial axes and A is the spectral information. Hyperspectral cameras are used with broadband halogen lights that produce the light source in full spectrum. Objects subjected to high values of light will produce light noise at higher range of the spectrum. This noise carries colour information that obscure chemical information. To help overcome this, a halogen light only at the higher range is produced by the subtraction of lower range light.

To help illustrate features of the method and system, several experiments are set forth below.

Experimental Methodology:
(a) Aflatoxin Infection on Almonds

Nonpareil variety of healthy almonds kernels were selected as samples which have good appearance and uniform size. Standard aflatoxin $B_1$ solutions of various concentrations ranging from 5 μg/mL to 50 μg/mL were prepared by diluting it with 50:50 methanol and water. 20 μL drops of aflatoxin solution was added onto the almond surface using a pipette to prepare almond samples each containing 0.1 μg/g to 1 μg/g of aflatoxin $B_1$ (considering the average weight of single almond is 1 g).

The samples were divided into four groups, namely 2.5, 5, 7.5 and 10 μg/g groups and healthy, noninfected almonds were considered as control for the experiments. The aflatoxin infested almonds were dried under natural air for drying of the methanol and water solution completely. Images of single almonds were scanned using a hyperspectral camera in the wavelength range of 900-1700 nm, one by one. Using 224 number of images of one almond at various wavelengths, the hyperspectral camera synthesized a hyperspectral image cube. The average spectra of each image were extracted after background removal and library of 3000 spectra was constructed. After capturing the images, the almond samples were destroyed, and aflatoxin content was verified using High Performance Liquid Chromatology (HPLC).

(b) Moisture Content Analysis

Nonpareil variety of healthy almonds kernels were selected as samples which have good appearance and uniform size. The sample bulk was divided into four groups. A measured amount of distilled water was added to the almonds to bring the moisture content from 6% to 12%. Almonds with 4% moisture content were used as control sample for the experiment. The moisture conditioned samples were stored in the refrigerator for 7 days to reach equilibrium. After 7 days, about 3000 images of various moisture content almonds were scanned and spectral library was generated. After capturing the images, all the almonds were verified for the actual moisture content using oven drying method.

(c) FFA and PV Value Analysis

Nonpareil variety of healthy almond bulk was divided into two groups, stored under 40° C. and 75% relative humidity for 1.5 months and 3 months, respectively to produce rancid almonds with higher FFA and PV value. Healthy almonds were used as control for the experiments. About 3000 images of various moisture content almonds were scanned and spectral library was generated. After capturing the images, all the almonds were verified for the actual FFA and PV content using standard titration method.

(d) Selection of Specific Wavelengths and Model Development

About 3000 images including the healthy and aflatoxin treated almonds of each parameter were captured for model development. The reference analysis data for moisture, FFA, PV, aflatoxin data and spectral data from the hyperspectral camera were used to develop a Partial Least Square Regression model (PLSR) to predict the respective quality parameters of the single almond. PLSR model assigned a weight to each of the 224 number of wavelengths based on predictability of aflatoxin content. Few wavelengths with higher weights were selected and used for training of the model again to check the accuracy. Validation of the model using the selected number of wavelengths was done against the sample outside the training data.

(e) Final Multispectral Imaging System Construction:

A pure shortwave infrared (SWIR) light was developed by the suppression of visible light from a halogen light source. Two SWIR multispectral camera with specific number of frequencies to capture a series of spectral images to assemble a spectral cube. A rotating glass system presents single almonds to the capture system, one at a time. Almonds flowing in single file trigger a light sensor, the advance spectral camera system acquires multiple times for each almond and converted to a series of short pulses for each wavelength required to capture. The cube capture is aligned and segmented to extract the corresponded frequencies for the respective almond in the frame. The average reflectance for each spectrum is calculated. The average spectrums of the wavelengths used (or displayed) to calculate the moisture, FFA, PV and aflatoxin content of a single almond.

The system and method described herein has many benefits and advantages. For example only, features of one or more embodiments described herein can generate an almond colour index, and even discern one or more of scratches, chips, stains, embedded shells, insect damage, mould, and other characteristics on almonds that could affect the quality of the almond.

The features described with respect to one embodiment may be applied to other embodiments or combined with or interchanged with the features of other embodiments, as appropriate, without departing from the scope of the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

U.S. Pat. No. 10,021,369 is hereby incorporated by reference herein in its entirety.

Definitions

Aflatoxins are poisonous carcinogens and mutagens that are produced by certain moulds (*Aspergillus flavus* and *Aspergillus parasiticus*) which grow in soil, decaying vegetation, hay, and grains.

Rancidity is the process of complete or incomplete oxidation or hydrolysis of moisture and/or oils when exposed to air, light, or humidity, resulting in unpleasant taste and odour. Pathways for rancidification include hydrolytic rancidity and oxidative rancidity.

Free fatty acids (FFA) are the by-product of hydrolytic rancidity and it is one of the parameters used for measuring rancidity in almonds.

Peroxide value (PV) are the by-products of oxidative rancidity. It is one of the parameters used for measuring rancidity in almonds.

SWIR light is reflective light; it bounces off objects much like visible light. Shortwave infrared (SWIR) light is typically defined as light in the 0.9-1.7 μm wavelength range but can also be classified from 0.7-2.5 μm. SWIR images are not in colour, making objects composition easily recognisable.

Spectral cube is a group of spectral images in which each layer is composed of an image taken in a specific wavelength. Like an RGB image where each layer of the three images represent the wavelengths of red, green, blue. Spectral cubes are composed of higher number of layers.

Spectra is the representation of the reflectance values of an image at various wavelengths.

Multispectral camera captures image data within few specific wavelength ranges across the electromagnetic spectrum.

What is claimed is:

1. A system for determining when a grain seed has an unsafe concentration of aflatoxin, comprising:
   a grain seed reservoir;
   a chute from said reservoir to a rotating glass disc;
   a plurality of light sources configured to emit a suppressed visible light upon each gain seed;
   a plurality of hyperspectral cameras configured to each capture a plurality of spectral images of each grain seed; and
   a processor configured to align and segment a spectral cube, determine an average reflectance for each spectral image, compare the average reflectance with a predetermined reflectance value indicative of a presence of an aflatoxin concentration designated to fail a predetermined health standard, and send instructions to a diverter to separate a grain seed determined to fail the health standard.

2. The system of claim 1, wherein the hyperspectral cameras are each configured to scan each grain seed using a wavelength of 900 to 1,700 nm.

3. The system of claim 1, wherein said processor is configured to assemble a spectral cube.

4. The system of claim 1, further comprising a rotating glass plate to present a plurality of the grain seeds in a single file array.

* * * * *